US008267890B2

(12) United States Patent
Alchas et al.

(10) Patent No.: US 8,267,890 B2
(45) Date of Patent: Sep. 18, 2012

(54) INTRADERMAL DELIVERY DEVICE WITH CONTOURED SKIN ENGAGING SURFACE GEOMETRY

(75) Inventors: Paul G. Alchas, Franklin Lakes, NJ (US); Peter W. Heyman, Florham Park, NJ (US); Marina S. Korisch, Wayne, NJ (US); William A. Easterbrook, Westwood, NJ (US); Robert E. West, Basking Ridge, NJ (US); Todd M. Chelak, Westboro, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 808 days.

(21) Appl. No.: 10/543,714

(22) PCT Filed: Jan. 30, 2004

(86) PCT No.: PCT/US2004/002699
§ 371 (c)(1),
(2), (4) Date: Feb. 12, 2007

(87) PCT Pub. No.: WO2004/069301
PCT Pub. Date: Aug. 19, 2004

(65) Prior Publication Data
US 2008/0045900 A1 Feb. 21, 2008

Related U.S. Application Data

(60) Provisional application No. 60/443,826, filed on Jan. 30, 2003.

(51) Int. Cl.
*A61B 17/34* (2006.01)

(52) U.S. Cl. .................................... 604/117; 604/115
(58) Field of Classification Search .................. 604/115, 604/117
See application file for complete search history.

(56) References Cited

U.S. PATENT DOCUMENTS 1,934,046 A  11/1933  Demarchi
(Continued)

FOREIGN PATENT DOCUMENTS

DE  958766 C  2/1957
(Continued)

OTHER PUBLICATIONS

Dermal Immune System by Brian J. Nickoloff, 1993.
(Continued)

*Primary Examiner* — Laura Bouchelle
(74) *Attorney, Agent, or Firm* — Robert E. West

(57) ABSTRACT

A medication delivery device, particularly an intradermal delivery device, having a needle cannula, with a sharpened distal end having a forward tip, and a limiter disposed about the needle cannula. The limiter has a distal end defining a skin engaging surface which is disposed transversely to, and at least partially about, the needle cannula. The skin engaging surface is generally non-flat with generally coplanar portions, and a recess being defined in the skin engaging surface which defines a void in or adjacent to the coplanar portions into which portions of a patient's skin can be deformed into when the skin engaging surface is pressed against the patient's skin. The forward tip of the needle cannula is spaced apart from a plane defined by the coplanar portions a distance ranging from about 0.5 mm to 3.0 mm such that the skin engaging surface limits penetration of the forward tip of the needle cannula to the dermis layer of the patient's skin.

9 Claims, 5 Drawing Sheets

U.S. PATENT DOCUMENTS

| | | | |
|---|---|---|---|
| 2,876,770 | A | 3/1959 | White |
| 3,073,306 | A | 1/1963 | Linder |
| 3,400,715 | A | 9/1968 | Pederson |
| 3,797,490 | A | 3/1974 | Hurschman |
| 4,270,537 | A | 6/1981 | Romaine |
| 4,373,526 | A | 2/1983 | Kling |
| 4,468,223 | A | 8/1984 | Minagawa et al. |
| 4,769,003 | A | 9/1988 | Stamler |
| 4,774,948 | A | 10/1988 | Markham |
| 4,834,704 | A | 5/1989 | Reinicke |
| 4,883,473 | A | 11/1989 | Thomas |
| 4,898,588 | A | 2/1990 | Roberts |
| 4,955,871 | A | 9/1990 | Thomas |
| 4,978,344 | A | 12/1990 | Dombrowski et al. |
| 5,137,516 | A | 8/1992 | Rand et al. |
| 5,141,496 | A | 8/1992 | Dalto et al. |
| 5,147,328 | A | 9/1992 | Dragosits et al. |
| 5,190,521 | A | 3/1993 | Hubbard et al. |
| 5,195,526 | A | 3/1993 | Michelson |
| 5,222,949 | A | 6/1993 | Kaldany |
| 5,417,662 | A | 5/1995 | Hjertman et al. |
| 5,505,694 | A | 4/1996 | Hubbard |
| 5,578,014 | A | 11/1996 | Erez et al. |
| 5,672,883 | A | 9/1997 | Reich |
| 5,873,856 | A | 2/1999 | Hjertman et al. |
| 5,921,963 | A | 7/1999 | Erez et al. |
| 6,099,504 | A | 8/2000 | Gross et al. |
| 6,200,291 | B1 | 3/2001 | Di Pietro |
| 6,203,529 | B1 | 3/2001 | Gabriel et al. |
| 6,210,369 | B1 | 4/2001 | Wilmot et al. |
| 6,494,865 | B1 | 12/2002 | Alchas |
| 6,569,143 | B2 | 5/2003 | Alchas et al. |
| 6,689,100 | B2 | 2/2004 | Connelly et al. |
| 6,808,506 | B2 | 10/2004 | Lastovich et al. |
| 6,843,781 | B2 | 1/2005 | Alchas et al. |
| 6,971,999 | B2 * | 12/2005 | Py et al. .................. 604/115 |
| 2001/0011171 | A1 | 8/2001 | Alchas et al. |
| 2001/0012925 | A1 | 8/2001 | Alchas et al. |
| 2002/0038111 | A1 | 3/2002 | Alchas et al. |
| 2002/0068909 | A1 | 6/2002 | Alchas et al. |
| 2002/0193740 | A1 | 12/2002 | Alchas et al. |
| 2003/0014018 | A1 | 1/2003 | Giambattista et al. |
| 2003/0199822 | A1 | 10/2003 | Alchas et al. |
| 2005/0033234 | A1 * | 2/2005 | Sadowski et al. ............. 604/140 |
| 2005/0113753 | A1 | 5/2005 | Alchas et al. |
| 2005/0256499 | A1 | 11/2005 | Pettis et al. |

FOREIGN PATENT DOCUMENTS

| | | |
|---|---|---|
| DE | 46325 C | 2/1989 |
| DE | 4127887 C1 | 1/1993 |
| DE | 29918794 | 2/2000 |
| EP | 0904790 A2 | 3/1999 |
| EP | 1066848 | 6/2000 |
| EP | 1092444 | 4/2001 |
| FR | 612401 A1 | 3/1987 |
| GB | 735538 | 8/1955 |
| GB | 2 206 794 A | 1/1989 |
| GB | 2321014 | 7/1998 |
| JP | H01-013862 | 3/1989 |
| JP | 2000-37456 | 2/2000 |
| WO | WO 93/09826 | 5/1993 |
| WO | WO 95/01198 | 1/1995 |
| WO | WO 99/25402 | 5/1999 |
| WO | WO 99/27986 | 6/1999 |
| WO | WO 99/34850 | 7/1999 |
| WO | WO 00/56384 | 9/2000 |
| WO | WO 02/083215 | 10/2002 |
| WO | 03/022330 | 3/2003 |
| WO | 03/066126 | 8/2003 |

OTHER PUBLICATIONS

Trials of Intradermal Hepatitis B Vaccine in Gambian Children by Whittle, Lam, Ryder, Jun. 1986.
The Dendritic Cell System and its Role in Immunogenicity by R. Steinman, 1991.
Intradermal Gene Immunization: The Possible Role of DNA Uptake in the Induction of Cellular Immunity to Viruses E Raz, et al., 1994.
Monographs of the Physiological Society No. 12: Substances Producing Pain and Itch by C.A. Keele et al., Jun. 2000.
Supplementary European Search Report for Application EP 04 70 6988, which is the EP filing of PCT/US2004002699, Oct. 2006.
PCT Search Report for PCT/US2004002699.
Laurent Pe, et al Vaccine 2007; 25:8833-42.

* cited by examiner

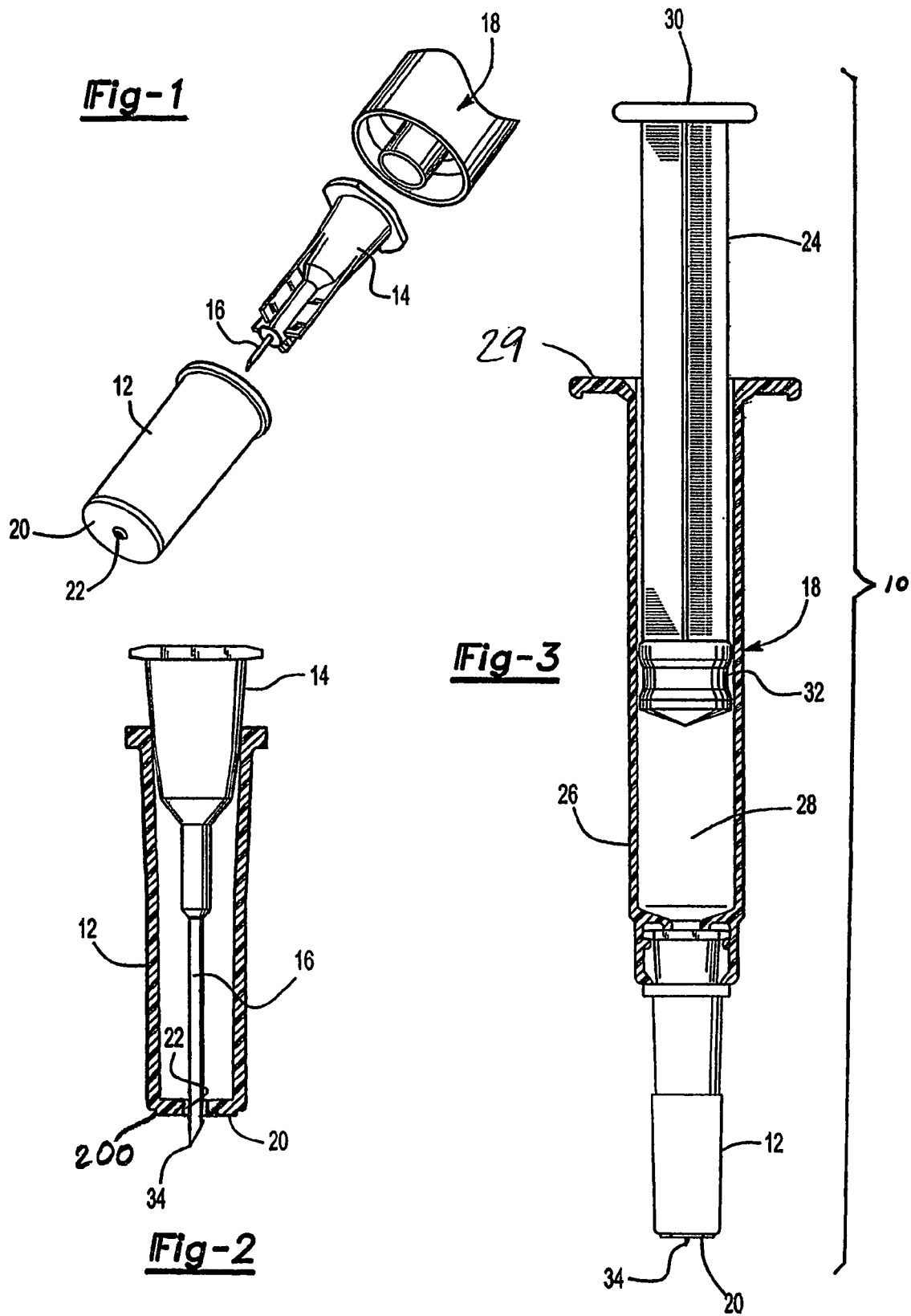

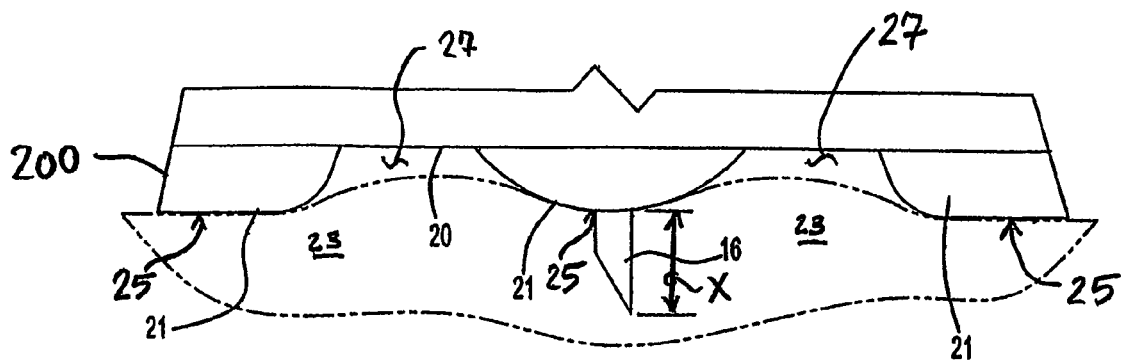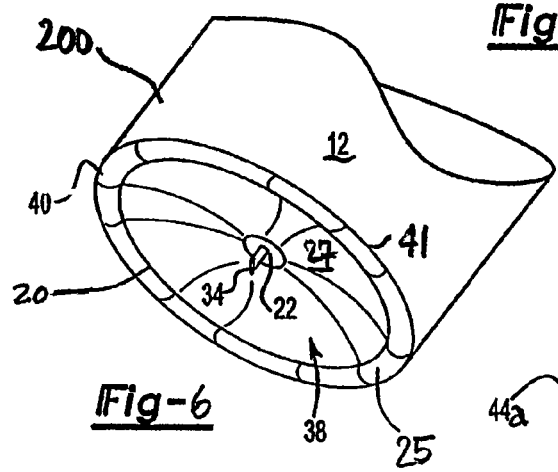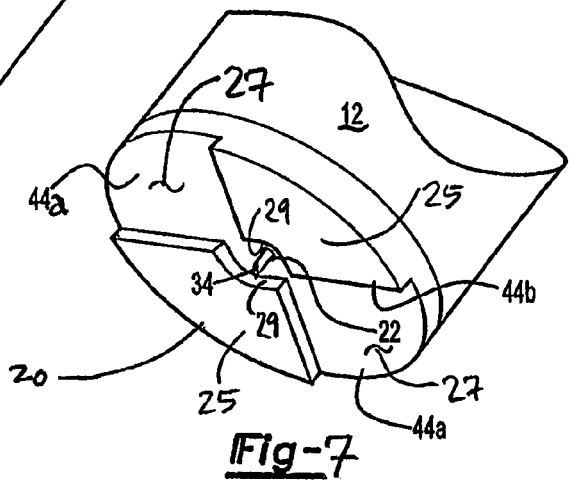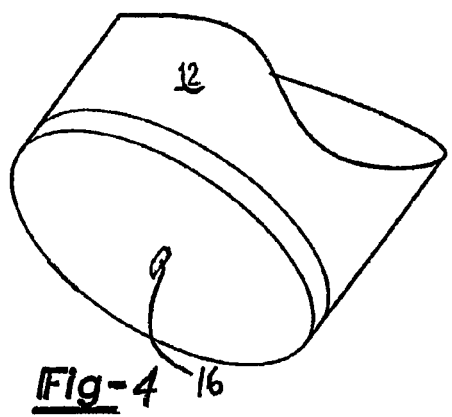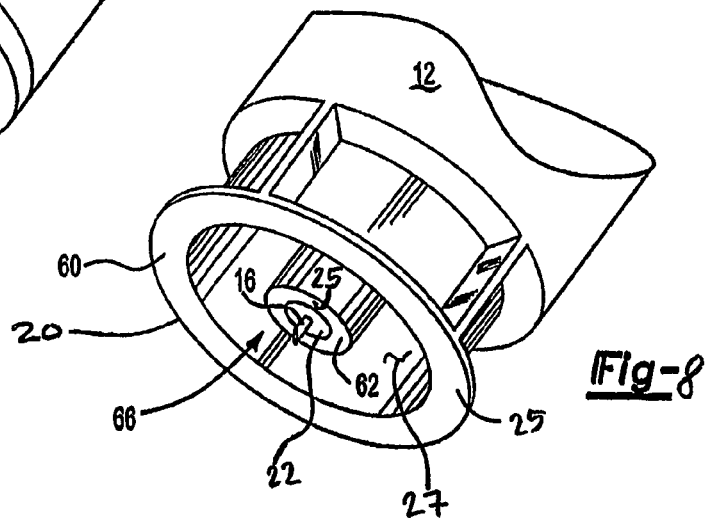

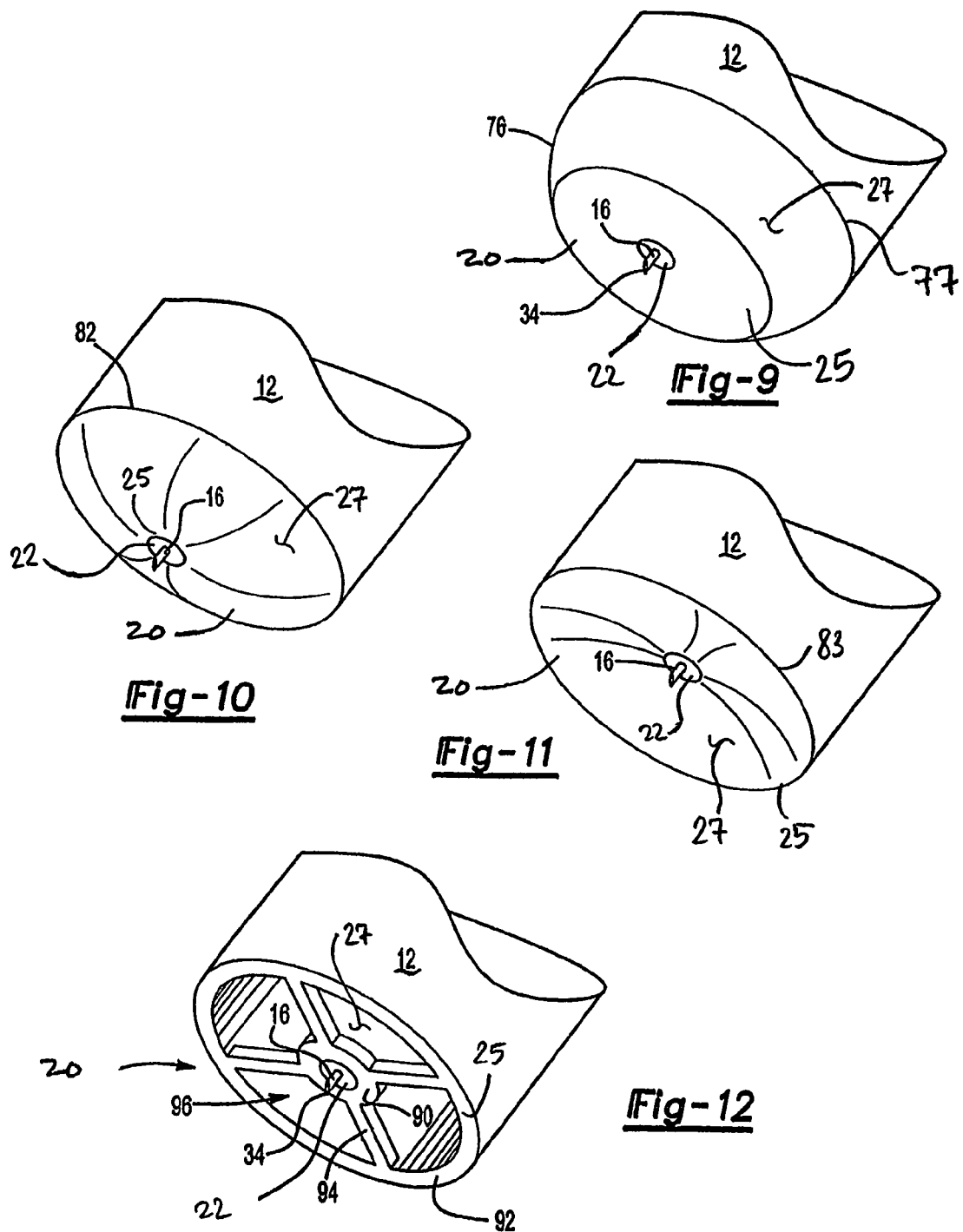

INTRADERMAL DELIVERY DEVICE WITH CONTOURED SKIN ENGAGING SURFACE GEOMETRY

CROSS-REFERENCE TO RELATED APPLICATIONS

This application claims priority to U.S. Provisional Application No. 60/443,826, filed on Jan. 30, 2003.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown that hepatitis B vaccines administered intradermally are more immunogenic than if administered intramuscularly. In addition, substances have been injected intradermally for diagnostic testing, such as, for example, using what is known in the art as the "Mantoux procedure" to determine immunity status of the animal against tuberculosis and immediate hypersensitivity status of type 1 allergic diseases.

An intradermal injection is made by delivering the substance into the dermis of a patient. Below the dermis layer is subcutaneous tissue (also sometimes referred to as the hypodermis layer) and muscle tissue, in that order. Generally, the outer skin layer, epidermis, has a thickness of between 50 to 200 microns, and the dermis, the inner and thicker layer of the skin, has a thickness between 1.5 to 3.5 millimeters. Therefore, a needle cannula that penetrates the skin deeper than about 3.0 millimeters has a potential of passing through the dermis layer of the skin and making the injection into the subcutaneous region, which may result in an insufficient immune response, especially where the substance to be delivered intradermally has not been indicated for subcutaneous injection.

The Mantoux procedure for making an intradermal injection is known to be difficult to perform, and therefore dependent upon experience and technique of the health care worker. Typically, the skin is stretched and a needle cannula is inserted into the skin at an angle varying from around 10 to 15 degrees relative to the plane of the skin. Once the cannula is inserted, fluid is injected to form a blister or wheal in the dermis in which the substance is deposited or otherwise contained. The formation of the wheal is critical to proper delivery of the substance into the intradermal layer of the skin. With the Mantoux procedure, the needle cannula may penetrate the skin at too shallow a depth to deliver the substance and result in what is commonly known in the art as "wet injection" because of reflux of the substance from the injection site.

An intradermal delivery device that enables administering an intradermal injection at a 90 degree angle to the skin of the patient is disclosed in U.S. Pat. No. 6,494,865. The intradermal delivery device disclosed in that patent provides a flat skin engaging surface (see, e.g., FIG. 1, reference character 20).

SUMMARY OF THE INVENTION

The present invention is directed to a medication delivery device, particularly an intradermal delivery device, having a needle cannula, with a sharpened distal end having a forward tip, and a limiter disposed about the needle cannula. The limiter has a distal end defining a skin engaging surface which is disposed transversely to, and at least partially about, the needle cannula. The skin engaging surface is generally non-flat with generally coplanar portions, and a recess being defined in the skin engaging surface which defines a void in or adjacent to the coplanar portions into which portions of a patient's skin can be deformed into when the skin engaging surface is pressed against the patient's skin. The forward tip of the needle cannula is spaced apart from a plane defined by the coplanar portions a distance ranging from about 0.5 mm to 3.0 mm such that the skin engaging surface limits penetration of the forward tip of the needle cannula to the dermis layer of the patient's skin.

The skin engaging surface generates uniform contact with the patient's skin during an intradermal injection, thereby facilitating successful injection and the formation of a wheal in the skin of the patient. The skin engaging surface of the subject invention has various configurations to depress the skin of the patient during administration of the intradermal injection. As a result of the depression of the skin, the skin is deformed. Advantageously, the deformation of the skin of the patient by the various configurations of the skin engaging surface is believed to enhance uniform contact with the skin of the patient and the formation of the wheal in the skin of the patient. It should be understood that different configurations of the invention may provide better skin contact, wheal formation and fluid delivery without leakage at different locations of the body of the patient, such as, for example, the hip, the shoulder, and the upper arm of the patient, depending upon the various skin thicknesses and the amount of muscle mass disposed in that location.

These and other features of the invention will be more fully understood from the following description of specific embodiments of the invention taken together with the accompanying drawings.

BRIEF DESCRIPTION OF THE DRAWINGS

FIG. 1 is an exploded perspective view of part of an intradermal delivery device in accordance with the present invention;

FIG. 2 is a partial cross-sectional view of the intradermal delivery device of FIG. 1;

FIG. 3 is a partial cross-sectional view of the intradermal delivery device of FIG. 1;

FIG. 4 is a perspective view of a skin engaging surface conformed to the exterior of a needle cannula;

FIG. 5 is a side view of a skin engaging surface of an intradermal delivery device in accordance with an embodiment of the present invention pressed against the skin of a patient;

FIGS. 6-15 are perspective views of various skin engaging surfaces in accordance with various embodiment of the present invention.

DETAILED DESCRIPTION OF THE INVENTION

Figure 13:
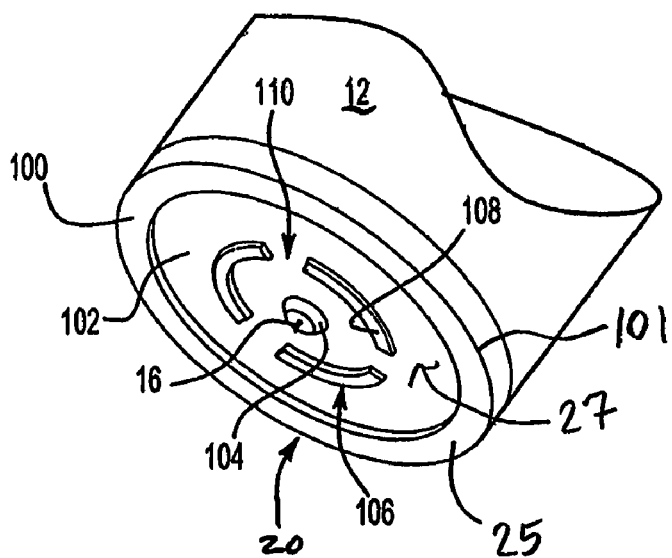

The present invention is directed to a medication delivery device, particularly, an intradermal delivery device having a skin engaging surface which generates tight contact with the skin during intradermal injection, thereby facilitating successful injection and the formation of a wheal in the skin of the patient being administered the intradermal injection. The skin engaging surface has various configurations to depress the skin of the patient, and apply pressure thereto, during administration of the intradermal injection. As a result of the depression of the skin, the skin is deformed. The deformation of the skin of the patient by the various configurations of the skin engaging surface is believed to enhance uniform contact with the skin of the patient and the formation of the wheal in the skin of the patient. The device may be used with any mammal, but it is expected to have most utility for human patients. It should also be understood that different configurations of the invention may provide better skin contact, wheal formation and fluid delivery without leakage at different locations of the body of the patient, such as, for example, the hip, the shoulder, and the upper arm of the patient, depending upon the various skin thicknesses and the amount of muscle mass disposed in that location.

Referring next to the drawings in detail, and with specific reference first to FIGS. 1-3, an intradermal delivery device in accordance with the present invention is there depicted and indicated generally by reference character 10. The delivery device 10 includes a limiter 12 secured, directly or indirectly, to the barrel or body 26 of a syringe 18. A flange 29 may be provided to encircle a proximal end of the body 26. The syringe body 26 may be formed of glass or plastic, and the syringe 18 may be of any known or later-discovered design. By way of non-limiting example, the syringe 18 depicted in FIG. 3 includes a plunger 24 slidably disposed within the syringe body 26 that defines a reservoir 28 that is in fluid communication with the needle cannula 16. The plunger 24 includes a thumb pad 30 that is depressible to expel a substance disposed within the reservoir 28 into the patient through the needle cannula 16. A stopper 32, sealingly and slidably disposed in the reservoir 28, is located on an opposite end of the plunger 24 from the thumb pad 30 as is known in the art. While a syringe is represented in FIG. 3, it should be understood that other injector devices such as, for example, pen needles, may also be used in the intradermal delivery device of the present invention.

Various configurations of the limiter 12 are possible, as will be recognized by those skilled in the art. As shown in FIGS. 1 and 2, the limiter 12 may be indirectly secured to the syringe 18 by being secured to a hub 14 of a needle cannula 16 which in turn is secured to the syringe 18. Here, the needle cannula 16 is supported by the hub 14 in any manner known in the art. The hub 14 may be connected to the syringe body 26 by a Luer fit or equivalent attachment method, or be formed unitarily with the syringe body 26. Alternatively, the limiter 12 may be directly fixed to the needle cannula 16 in acting as a hub of the needle cannula 16 and formed to be connected to the syringe body 26 by a Luer fit or equivalent attachment method. As a further variation, the needle cannula 16 maybe directly fixed or "staked" to the syringe body 26 without the hub 14 and with the limiter 12 being directly connected to the syringe body 26 by a snap-fit, friction fit, adhesive or other bond, or by any other connection method. In any regard, the limiter 12 is separately formed from the syringe body 26. Also, it is preferred that the limiter 12 be formed of plastic.

The limiter 12 may include an aperture 22 through which the needle cannula 16 may extend. Advantageously, with this arrangement, the needle cannula 16 may be formed of a standard length (e.g., for subcutaneous or deeper injection) with only a pre-determined length of the needle cannula 16 being exposed for intradermal injection and the remainder of the needle cannula 16 being housed within the body of the limiter 12. Alternatively, the needle cannula 16 may be formed to the desired length (e.g., intradermal length) and affixed directly to the limiter 12. Here, the needle cannula 16 may extend through, and be directly affixed to, the aperture 22 with the aperture 22 substantially conforming to the exterior of the needle cannula 16 (e.g., the respective surface may be molded about the needle cannula 16); also, the aperture 22 can be of limited depth (i.e., be blind) or extend fully through the surface (i.e., be a through hole) of the limiter 12. Alternatively, the needle cannula 16 may be directly fixed to the limiter 12 without any aperture 22 being used (i.e., the needle cannula 16 can be fixed to an external portion of the limiter 12). With either arrangement (an aperture being or not being used), no gap need be formed between the needle cannula 16 and the surrounding portions of the respective surface. For example, FIG. 4 shows the needle cannula 16 being fixed to the limiter 12 without any gaps between the needle 16 and the surrounding portions of the limiter 12. If desired, a gap may be provided between the needle cannula 16 and the surrounding surface portions, as shown in other Figures, to accommodate passage of the needle cannula 16 through the respective surface without any fixation therebetween. For example, as shown in FIG. 2, the needle cannula 16 may be supported by the hub 14 and may pass through the limiter 12 without being fixed thereto.

The specific manner of fixation of the limiter 12 and/or the needle cannula 16 and whether or not the needle cannula 16 extends through the limiter 12 are not critical features of the subject invention. More specifically, regardless of how the limiter 12, the hub 14, the syringe body 26, and the needle cannula 16 are formed or attached, the delivery device 10 includes a skin engaging surface 20 that is defined on the limiter 12 and is disposed transversely, preferably generally perpendicularly, to the needle cannula 16 with a distal tip 34 of the needle cannula 16 extending from the skin engaging surface 20 a predetermined intradermal delivery distance, preferably a distance ranging from approximately 0.5 to approximately 3.0 millimeters. For illustrative purposes, the skin engaging surface 20 is shown and discussed herein in conjunction with the limiter 12. It is to be understood, however, that in accordance with the discussion set forth above, the skin engaging surface 20 may be defined on the hub 14 acting as the limiter 12.

As shown in FIGS. 5-15, the skin engaging surface 20 may be contoured, non-continuous, or otherwise non-flat. As a general example, and as shown in FIG. 5, the skin engaging surface 20 may include several protuberances 21 that define generally coplanar surface portions 25 that contact a mammal's skin 23 and cause the skin 23 to deform upon being pressed thereagainst. One or more recesses 27 are defined in the skin engaging surface 20 to define voids into which displaced skin can be deformed. Thus, the skin 23 of the patient may be deformed by the protuberances 21 and displaced into the recesses 27 between the protuberances 21 if excess gathered skin is present. The targeted deformation and stretching of the patient's skin by the skin engaging surface 20 assists the successful intradermal delivery of the entire fluid dose without leakage and in the formation of a wheal.

Referring next to FIGS. 6-15, various other embodiments of the present invention are depicted and will now be discussed in detail. Referring first to FIG. 6, a generally concave skin engaging surface 20 is depicted. In this embodiment, the skin engaging surface 20 includes a generally concave central area 38 where the distal tip 34 of the needle cannula 16 extends from the center thereof. The concave area 38 is at least partially bounded by a perimeter 41 positioned forward or distally of the concave area 38. A rim 40 is interposed between the perimeter 41 and the concave area 38. The coplanar surface portions 25 are defined on the rim 40 which contact a patient's skin, while the recesses 27 are defined adjacent to the central area 38 and within the perimeter 41. The rim 40 may be flat, or, as shown in FIG. 6, convex. If the rim 40 is not flat, the recesses 27 may be defined over portions of the rim 40 which are not distalmost portions of the skin engaging surface 20—i.e., portions of the rim 40 which are recessed back from distalmost portions of the rim 40. The skin of a patient may be deformed and pushed into the recesses 27 by the rim 40 toward the needle cannula 16 during administration of the intradermal injection. Central aperture 22 may be provided through which the needle cannula 16 may extend.

With reference next to FIG. 7, another embodiment of the present invention is depicted. The skin engaging surface 20 depicted in FIG. 7 has stepped and pie-shaped sections 44a and 44b, which alternate between a rearward or proximal height (44a) and a forward or distal height (44b). The coplanar portions 25 are defined on the pie-shaped sections 44b, whereas, the recesses 27 are defined between the pie-shaped sections 44b (and at least partially above the pie-shaped sections 44a). Therefore, the skin of the patient may be deformed into the recesses 27 defined by the rearward height 44a, and stretched by the coplanar portions 25 defined by the forward height 44b. The pie-shaped sections 44b may be tuncated to have edges 29 spaced from the needle cannula 16. With the edges 29 being arcuate as shown in FIG. 7, a continuous and generally bow-tie shaped recess 27 may be defined between the sections 44b and about the needle cannula 16. The aperture 22 may also be provided through which the needle cannula 16 may extend.

Referring now to FIG. 8, a still further alternate embodiment of the present invention is depicted in which the skin engaging surface 20 is defined by a generally flat peripheral rim 60 and a generally flat central rim 62 concentrically aligned with peripheral rim 60 and separated by an annular recess 27. The needle cannula 16 extends from the central rim 62. The coplanar portions 25 are defined on the peripheral rim 60 and/or the central rim 62 depending on the relative heights of the elements. Preferably, and as shown, the peripheral rim 60 and the central rim 62 are disposed on generally the same plane and, thus, the coplanar portions 25 would be defined on both elements. However, it should be understood that the present invention also contemplates that the central rim 62 may be positioned on a plane offset from the plane defined by the peripheral rim 60 (i.e., the peripheral rim 60 may be located distally of the central rim 62 or vice versa). In this case, the coplanar portions 25 are preferably defined on the distalmost surfaces of the skin engaging surface 20 whether they be defined on the peripheral rim 60 or the central rim 62. Also, the recess 27 may extend above the offset and proximal surfaces (i.e., the surfaces which are not distalmost) of the peripheral rim 60 or the central rim 62. While administering the intradermal injection, the skin of the patient is deformed into the annular recess 27 and stretched by the coplanar portions 25 of the peripheral rim 60 and/or the central rim 62. An aperture 22 may also be defined in the skin engaging surface 20 through which the needle cannula 16 may extend.

A still further alternate embodiment of the present invention is depicted in FIG. 9. The skin engaging surface 20 includes a generally planar portion with the needle cannula 16 extending therefrom. The coplanar portions 25 are defined about the needle cannula 16 on the planar portion of the skin engaging surface 20. The skin engaging surface 20 also includes a radiused perimeter 76 that bounds the coplanar portions 25 and transitions gradually away therefrom to perimeter 77. The radiused perimeter 76 defines the recesses 27 about the coplanar portions 25. Therefore, the skin engaging surface 20 stretches the skin of the patient outwardly away from the injection site while administering the intradermal injection, and the radiused perimeter 76 provides a gradual transitional area with the recesses 27 into which the skin may deform to ease the depression of the skin by the skin engaging surface 20. In addition, aperture 22 may be defined in the skin engaging surface 20 through which the needle cannula 16 may extend.

Referring now to FIG. 10, a still further alternate embodiment of the present invention is depicted in which the skin engaging surface 20 comprises a generally convex configuration. The skin engaging surface 20 is generally convex with the needle cannula 16 being located centrally therewithin. Coplanar portions 25 are defined at the limit of the skin engaging surface 20 closest to the needle cannula 16. Similarly to the embodiment of FIG. 9, the convex skin engaging surface 20 gradually transitions proximally to perimeter 82 in defining the recesses 27 about the coplanar portions 25. With this embodiment, the skin of the patient is stretched outwardly and away from the injection site while administering the intradermal injection. The amount of stretching is reduced moving away from the needle cannula 16 (i.e., away from the center of the skin engaging surface 20), and is minimal at the perimeter 82 of the skin engaging surface 20 due to the convex configuration which locates the perimeter 82 of the skin engaging surface 20 rearward from the exposed needle cannula 16. An aperture 22 may be defined through the skin engaging surface 20 through which the needle cannula 16 may extend.

Referring to FIG. 11, a still further embodiment of the present invention is depicted in which the skin engaging surface 20 is generally concave. In contrast to the embodiment of FIG. 6, no rim is provided here. Coplanar portions 25 are defined along perimeter 83 with recesses 27 being defined by the concave engaging surface 20 within the perimeter 83. In use, the skin of the patient deforms and is forced inwardly toward the needle cannula 16 by the concave configuration of the skin engaging surface 20. Aperture 22 may be provided through which the needle cannula 16 may extend.

Referring now to FIG. 12, a still further embodiment of the present invention is depicted in which skin the engaging surface 20 defines concentrically aligned inner and outer rims 90, 92, connected by one or more spokes 94 extending therebetween. Preferably four spokes 94 extend between the inner and outer rims 90, 92. However, fewer or more spokes 94 may be included as desired. Coplanar portions 25 may be defined on the inner rim 90, the outer 92 rim, and/or any of the spokes 94 depending on the relative heights of the elements. The recesses 27 are at least defined between the spokes 94 and the inner and outer rims 90, 92 and may be defined above some of these elements depending on their relative heights. The inner rim 90 may also define an aperture 22 axially aligned with the needle cannula 16 through which the needle cannula 16 passes. While administering the intradermal injection, skin is deformed in the recesses 27 and is stretched by the central portions 25. Preferably, all distal-facing surfaces of the inner rim 90, the outer rim 92, and the spokes 94 are generally coplanar and, thus, the coplanar portions 25 are defined on each of those elements also.

Referring now to FIG. 13, yet another alternative embodiment of the present invention is depicted in which the skin engaging surface 20 is defined by an outer rim 100 that encircles a central surface 102. The central surface 102 is disposed rearward or proximally of the outer rim 100. The outer rim 100 may be either flat or slightly convex. The needle cannula 16 extends outwardly from the skin engaging surface 20 and is immediately surrounded by a protuberance 104 having a blister or bubble like shape. A broken ring 106 may be provided concentrically aligned between the protuberance 104 and the outer rim 100. The broken ring 106 includes a plurality of spaced members 108 each being separated by a space 110. The spaced members 108 extend upwardly from the central surface 102 to a plane generally the same as or slightly below a plane defined by the outer rim 100. The coplanar portions 25 may be defined on the outer rim 100, the protuberance 104, and/or the spaced members 108 depending on the relative heights of the elements. It is preferred that the coplanar portions 25 be defined on the distalmost portions of the skin engaging surface 20, be it that those portions are defined on the outer rim 100, the protuberance 104, and/or the spaced members 108. The recesses 27 are defined within perimeter 101 of the skin engaging surface 20, and depending on the relative heights of the rim 100, the protuberance 104 and/or the spaced members 108, the recesses 27 may or may not be defined above those elements. During administration of the intradermal injection, the skin of the patient gathers in the recesses 27. Further, the skin may be stretched by the protuberance 104, the spaced members 108, and/or the outer rim 100. If the broken ring 106 is not provided, the skin engaging surface 20 generally has the cross-section shown in FIG. 5 and discussed above. An aperture may also be provided through which the needle cannula 16 extends.

Figure 14:
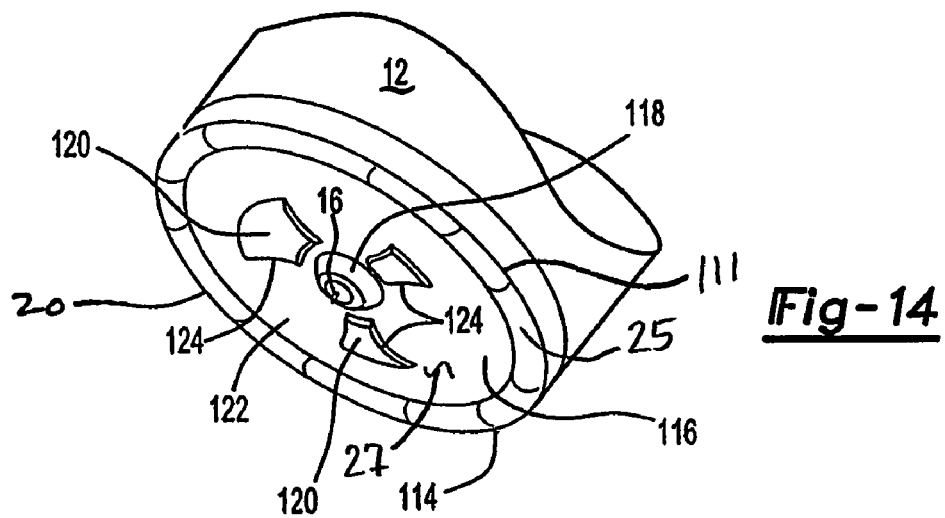

Referring now to FIG. 14, still another embodiment of the present invention is depicted in which the skin engaging surface 20 is defined by an outer rim 114 that transitions to a central surface 116. The central surface 116 may be formed with various configurations, such as being flat or convex. The needle cannula 16 extends outwardly away from the skin engaging surface 20 and is immediately surrounded by a protuberance 118 having a blister or bubble like shape. A plurality of arcuate protuberances 120 encircle the central protuberance 118 and are concentrically aligned between the inner protuberance 118 and the outer rim 114. The outer rim 114 may be flat or convex. A space 122 is defined between each arcuate protuberance 120. Each arcuate protuberance 120 includes a wall 124 opposing the adjacent protuberance 120. Each wall 124 preferably defines a convex surface, but may be formed with other configurations such as being flat. The coplanar portions 25 may be defined on the outer rim 114, the protuberance 118, and/or the arcuate protuberances 120 depending on the relative heights of the elements. It is preferred that the coplanar portions 25 be defined on the distalmost portions of the skin engaging surface 20, be it that those portions are defined on the outer rim 114, the protuberance 118 and/or the arcuate protuberances 120. The recesses 27 are defined within perimeter 111 of the skin engaging surface 20, and depending on the relative heights of the rim 114, the protuberances 118 and/or the arcuate protuberances 120, the recesses 27 may or may not be defined above those elements. While administering the intradermal injection, the skin of the patient gathers in the recesses 27. Also, the skin may be stretched by the central protuberance 118, the arcuate protuberances 120, and/or the outer rim 114. An aperture may also be provided through which the needle cannula 16 extends.

Figure 15:
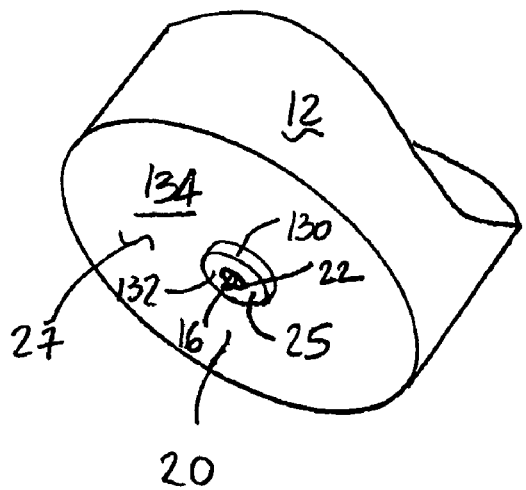

In a preferred embodiment, and with reference to FIG. 15, the skin engaging surface 20 includes an annular protrusion 130 which encircles the needle cannula 16. The coplanar portions 25 are defined on a free distal end 132 of the protrusion 130, particularly the distalmost portions of the free distal end 132. It is preferred that the protrusion 130 bound the aperture 22, if used to accommodate the needle cannula 16. The skin engaging surface 20 also includes a secondary surface portion 134 which extends radially from the protrusion 130, above which the recesses 27 are defined. The secondary surface portion 134 may be generally flat, as shown in FIG. 15, or be contoured, e.g., tapered to diverge in a distal to proximal direction. The secondary surface 134 is setback from the free distal end 132.

Figure 16A:
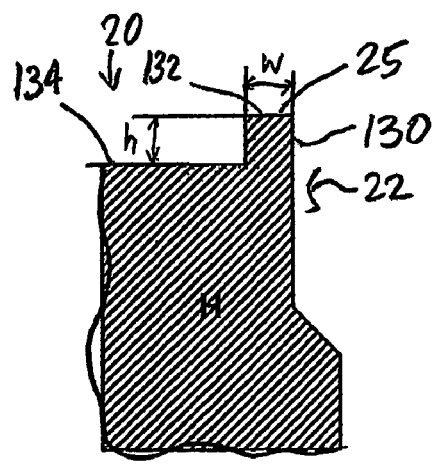
FIGS. 16a-16c are various cross-sections useable with the protrusion of the embodiment of FIG. 15.
Figure 16B:
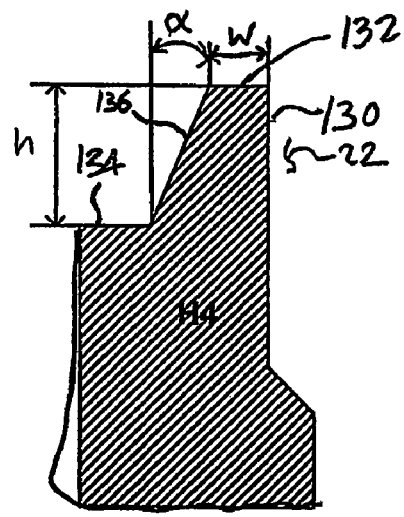
Figure 16C:
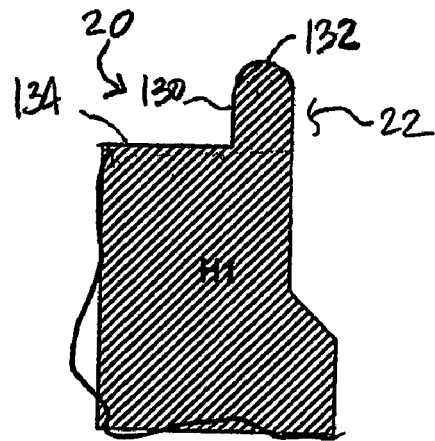

The free distal end 132 may be formed generally planar or with other configurations. As such, the free distal end 132 may define the coplanar portions 25 continuously or discontinuously about the needle cannula 16. In addition, and as shown in FIGS. 16a-16c, the protrusion 130 may be formed with various cross-sections, including rectangular and trapezoidal, although a square cross-section is most preferred. Other polygonal shapes are possible. Also, the protrusion 130 may be at least partially formed arcuately, as shown in FIG. 16c.

With a rectangular cross-section as shown in FIG. 16a, the height h of the protrusion 130 may be in the range of 0.2 mm to 0.5 mm and the width w of the free distal end 132 may be in the range of 0.2 mm to 0.5 mm. Of course, with a square cross-section, the height h and the width w are generally equal. With reference to FIG. 16b, and with a trapezoidal cross-section, the protrusion 130 may have a height h in the range of 0.5 mm to 1.0 mm, a width w of the free distal end 132 in the range of 0.35 mm to 0.6 mm, and a side surface 136 disposed at an angle $\alpha$, the angle $\alpha$ being in the range of 30-45 degrees.

As indicated above, the various embodiments of the present invention depicted in FIGS. 1-15 are not limited for use with syringes and may be used in connection with any injection device suitable for delivering drug substances to the intradermal region of the skin.

As will be appreciated by those skilled in the art, embodiments of the skin engaging surface 20 rely on skin being deformed into at least the recesses 27 defined within the perimeter of the skin engaging surface 20. The recesses 27 may be in direct communication with the aperture 22 through which the needle cannula 16 passes (e.g., as shown in FIGS. 6 and 11) or may be spaced from the aperture 22 (e.g., with reference to FIG. 8, the annular space between the rims 60 and 62 is spaced from the aperture 22). Beyond the perimeter of the skin engaging surface 20, a dramatic transition exists to a different oriented surface, such as the cylindrical body of the limiter 12. With the skin engaging surfaces 20 that have gradual transition portions (such as those shown in FIGS. 9 and 10), the gradual transition portions generally face in the same direction as the remaining portions of the skin engaging surface 20. Beyond the perimeters 77 and 82 of the gradual-transition embodiments, a dramatic transition is present to a secondary external surface (e.g., external surface 200 shown in FIGS. 2, 5 and 6) which faces in one or more general directions different from that in which the skin engaging surface 20 faces (e.g., the cylindrical side wall of the limiter 12).

It is preferred that the coplanar portions 25 be located on the distal most portions of the skin engaging surface 20 for the embodiments that include such. It is also preferred that the distal tip 34 of the needle cannula 16 be located a distance ranging from 0.5 to 3.0 millimeters from the coplanar portions 25. With reference to FIG. 5, and by way of non-limiting example, distance X from the coplanar portions to the tip of the needle cannula is preferably in the range of 0.5 to 3.0 millimeters.

It is further preferred that skin engaging portions of the skin engaging surface 20 be located about the needle cannula 16 such that an even ring of pressure can be generated about the needle cannula 16 during intradermal injection. Thus, the coplanar portions 25 are preferably located continuously or discontinuously about the needle cannula 16 to coact and provide an even ring of pressure during injection. It is further preferred that the ring of pressure be spaced from the needle cannula 16 to facilitate wheal formation.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A medication delivery device comprising:
a needle cannula having a sharpened distal end having a forward tip; and,
a limiter disposed about said needle cannula and having a distal end defining a skin engaging surface disposed transversely to, and at least partially about, said needle cannula, said skin engaging surface being generally non-flat,
a recess being defined in said skin engaging surface which defines a void into which portions of a patient's skin can be contoured into when said
skin engaging surface is pressed against the patient's skin, said forward tip of said needle cannula being spaced apart from a plane a pre-selected and fixed distance ranging from about 0.5 mm to 3.0 mm such that said skin engaging surface limits penetration of said forward tip of said needle cannula to the dermis layer of the patient's skin wherein said skin engaging surface includes a continuous annular protrusion extending distally wherein said protrusion has a height ranging from 0.2 to 1.0 mm and said protrusion is bound to said recess, said protrusion terminating at a proximal free end, said proximal free end defining a width ranging from 0.2 to 0.6 mm.

2. A device as in claim 1, wherein said protrusion terminates in a free distal end, said coplanar portions being defined on said free distal end.

3. A device as in claim 1, wherein said protrusion encircles said needle cannula.

4. A device as in claim 1, wherein at least a portion of the cross-section of said protrusion is arcuate.

5. A device as in claim 1, wherein said first portion is generally annular and encircles said protrusion.

6. A medication delivery device comprising:
a needle cannula having a sharpened distal end having a forward tip; and,
a limiter disposed about said needle cannula and having a distal end defining a skin engaging surface disposed transversely to, and at least partially about, said needle cannula, said skin engaging surface being generally non-flat,
a recess being defined in said skin engaging surface which defines a void into which portions of a patient's skin can be contoured into when said skin engaging surface is pressed against the patient's skin, said forward tip of said needle cannula being spaced apart from said skin engaging surface a distance ranging from about 0.5 mm to 3.0 mm such that said skin engaging surface limits penetration of said forward tip of said needle cannula to the dermis layer of the patient's skin
wherein said skin engaging surface includes a first portion and a continuous annular protrusion extending distally from said first portion and said protrusion is bound to said recess and at least a portion of the cross-section of said protrusion is arcuate wherein said protrusion has a height ranging from 0.5 to 1.0 mm, said protrusion terminating at a distal free end, said proximal free end defining a width ranging from 0.35 mm to 0.6 mm.

7. A device as in claim 6, wherein said protrusion has a generally rectangular cross-section.

8. A device as in claim 6, wherein said protrusion has a generally trapezoidal cross-section.

9. A device as in claim 6, wherein said protrusion has a generally square cross-section.

* * * * *